US010045757B2

(12) United States Patent
Brown (10) Patent No.: US 10,045,757 B2
(45) Date of Patent: Aug. 14, 2018

(54) GUARDED IMAGING DEVICES AND METHODS (71) Applicant: Volcano Corporation, San Diego, CA (US)

(72) Inventor: Jeffery H. Brown, Valley Center, CA (US)

(73) Assignee: Volcano Corporation, San Diego, CA (US)

( * ) Notice: Subject to any disclaimer, the term of this patent is extended or adjusted under 35 U.S.C. 154(b) by 1209 days.

(21) Appl. No.: 14/135,359

(22) Filed: Dec. 19, 2013

(65) Prior Publication Data
US 2014/0180079 A1  Jun. 26, 2014

Related U.S. Application Data (60) Provisional application No. 61/740,994, filed on Dec. 21, 2012.

(51) Int. Cl.
A61B 8/00 (2006.01)
A61B 8/12 (2006.01)
A61B 5/00 (2006.01)
A61B 5/02 (2006.01)

(52) U.S. Cl.
CPC .............. *A61B 8/12* (2013.01); *A61B 5/0066* (2013.01); *A61B 5/0084* (2013.01); *A61B 5/0095* (2013.01); *A61B 5/02007* (2013.01); *A61B 5/4839* (2013.01); *A61B 5/6853* (2013.01); *Y10T 29/49826* (2015.01)

(58) Field of Classification Search
CPC combination set(s) only.
See application file for complete search history.

(56) References Cited

U.S. PATENT DOCUMENTS

| | | | |
|---|---|---|---|
| 7,539,531 B2* | 5/2009 | Camus | A61B 5/0066 600/470 |
| 2005/0222596 A1* | 10/2005 | Maschke | A61B 17/32072 606/159 |
| 2007/0066888 A1* | 3/2007 | Maschke | A61B 34/20 600/424 |
| 2008/0161696 A1* | 7/2008 | Schmitt | A61B 5/0066 600/467 |
| 2009/0076448 A1* | 3/2009 | Consigny | A61B 17/22 604/103.01 |
| 2010/0100087 A1* | 4/2010 | Mazzone | A61B 18/02 606/21 |
| 2011/0208022 A1* | 8/2011 | Brawer | A61B 10/0045 600/309 |

(Continued)

OTHER PUBLICATIONS

Dillow, Clay, "Injecting Oxygen Directly into the Bloodstream Could Save Suffocating Patients", Jun. 27, 2012.*

*Primary Examiner* — Christopher Cook (57) ABSTRACT

An integrated therapeutic and imaging device that uses at least two balloons to provide a guarded zone that can be evacuated and replaced with a fluid that is sufficiently clear to permit optical coherence tomography (or even high resolution ultrasound) imaging that would otherwise be of poor quality or impossible. Methods of making and operating the imaging device to obtain clear, high quality images, as well as treating a patient's tissue with the device within a living body in association with obtaining an image of the patient's tissue, are included.

36 Claims, 4 Drawing Sheets (56) References Cited

U.S. PATENT DOCUMENTS

2011/0224655 A1* 9/2011 Asirvatham .......... A61M 1/101
  606/1
2012/0143099 A1* 6/2012 Daniels .............. A61B 18/1492
  601/2

* cited by examiner

GUARDED IMAGING DEVICES AND METHODS

CROSS-REFERENCE TO RELATED APPLICATION

The present application claims the benefit of the filing date of provisional U.S. Patent Application No. 61/740,994 filed Dec. 21, 2012. The entire disclosure of this provisional application is incorporated herein by this reference.

TECHNICAL FIELD

Embodiments of the present disclosure relate generally to the field of medical devices and, more particularly, to flexible, elongate bodies (e.g., a catheter) including imaging within a guarded zone between two inflatable balloon assemblies, along with methods of making and using such devices and systems including such devices within a living body.

BACKGROUND

Intravascular imaging systems are widely used in interventional cardiology as a diagnostic tool for a diseased vessel, such as an artery, within the human body. Various sensors may be placed on a catheter and positioned in the body. One type of imaging system is an intravascular ultrasound (IVUS) system, which can include either a single rotating transducer or a solid-state array of transducers.

Intravascular imaging systems are often used to detect occlusions or other materials in an artery or other vessels, which can sometimes be relieved through use of a balloon catheter or other means. A balloon catheter is a type of catheter with a balloon near the tip. The balloon catheter is designed to be inserted into a patient's artery or vessel, and positioned near a spot where an occlusion was detected through use of an intravascular imaging system. Upon reaching the detected occlusion, the balloon is inflated to relieve the occlusion. In some instances, the balloon catheter includes a stent, and inflation of the balloon expands and deploys the stent within the vessel.

While existing catheters deliver useful diagnostic imaging information, there is a need for enhanced image quality and ease of use to provide more valuable insight into the condition of vessels and passageways in vivo. Accordingly, there remains a need for improved catheter-type devices, systems, and methods for providing a superior imaging device with clearer images by having fewer and smaller distortions, or speckles, compared to those presently available. Moreover, there is a need for imaging systems that are also capable of treating a patient's vessel in conjunction with monitoring the course of treatment, and for extending the time available to conduct more in-depth imaging or treatment, or both.

SUMMARY

The disclosure relates to an imaging device, and in some embodiments, an integrated imaging and treatment device, that provides two balloon assemblies that define a guarded zone between the balloons to conduct imaging, treatment, or both. Alternatively, the imaging may occur in this guarded zone while treatment occurs distal to both balloons.

In a first aspect, the disclosure encompasses an imaging device having a proximal portion and proximal end, and a distal portion and distal end, which includes: a first balloon assembly in a distal position, which includes a first balloon, and a first connection lumen that extends from the proximal portion into the first balloon to permit transfer of a fluid therebetween so as to independently inflate or deflate the first balloon; a second balloon assembly in a proximal position relative to the first balloon assembly, which second balloon assembly includes a second balloon; and a second connection lumen that extends from the proximal portion into the second balloon to permit transfer of a fluid therebetween so as to independently inflate or deflate the second balloon; a guarded zone disposed between the first and second balloon assemblies that is coupled to at least a first guarded zone lumen that extends from the guarded zone to the proximal portion; an imaging component that is disposed in the guarded zone and that is configured to image an adjacent tissue zone of a patient; and a flexible, elongate body joining at least the first and second balloon assemblies, the guarded zone, and the imaging component. In a preferred embodiment, the device further includes a guidewire lumen that extends from the distal portion to at least a position distal to the second balloon assembly.

In one embodiment, the imaging component is coupled to a connection media lumen that extends from the proximal portion to a second position within the guarded zone. In a preferred embodiment, the connection media lumen encompasses at least one electrical conduction wire either to provide electrical power to the imaging component, to transmit data signals between the imaging component and the proximal portion, or both. In another embodiment, the imaging device further includes a second guarded zone lumen wherein the first guarded zone lumen permits transfer of a fluid into the guarded zone and the second guarded zone lumen permits transfer of a fluid from the guarded zone to a position distal to at least one of the first and second balloons. In a preferred embodiment, the imaging component includes at least a portion of an optical coherence tomography device including an optical fiber or reflector and further including an optical fiber disposed in the connection media lumen. In a more preferred embodiment, the imaging component includes at least one ultrasound transducer. In another more preferred embodiment, the ultrasound transducer is adapted to operate in a high frequency range of about 40 MHz to about 80 MHz.

In another embodiment, the first guarded zone lumen is adapted to deliver a therapeutic or diagnostic agent to the tissue zone. In another embodiment, the imaging device further includes an ablation device disposed in the guarded zone. In yet another embodiment, the imaging device further includes a distal port lumen that extends from the proximate portion to a position distal the first and second balloon assemblies. In another embodiment, the distal port lumen is configured to deliver a therapeutic or diagnostic agent to the distal end when at least one of the first and second balloons is inflated.

In a second aspect, the disclosure encompasses methods for imaging a tissue zone in a patient including by inserting from a proximal zone, a flexible, elongate body including first and second inflatable zones that are inflatable in vivo and an imaging component disposed in a guarded zone defined by a region between the first and second inflatable zones, to a distal position adjacent a tissue zone to be imaged; providing through an irrigation lumen, which extends between the proximal zone and the guarded zone, an imaging fluid that is adapted to conduct a signal therethrough that is emitted by the imaging component; and obtaining an image of the tissue zone with the imaging component.

In one embodiment, the image is obtained by selecting optical coherence tomography or high-resolution ultrasound imaging at a frequency range of about 40 MHz to about 80 MHz. In another embodiment, the method includes rotating a portion of the imaging component, i.e., a rotational element. In another embodiment, the method includes a phased-array, for example, by having the imaging component selected to include a phased-array. In a preferred embodiment, at least one of the images obtained does not contain visible distortion at normal magnification.

In another embodiment, the obtaining the image is repeatedly conducted as the flexible, elongate body is advanced so that the imaging component is adjacent to one or more additional tissue zones. In one embodiment, the method further includes treating the tissue zone by providing at least one therapeutic agent through a treatment lumen that extends from the proximal zone to the guarded zone. In a preferred embodiment, the treating is concurrent with the obtaining an image. In another preferred embodiment, the method further includes analyzing an obtained image to identify a dissolvable material in the tissue zone, and selecting the at least one therapeutic agent to treat the dissolvable material. In yet a further preferred embodiment, the method further includes repeating the analyzing, selecting, and treating to remove a plurality of dissolvable materials from the tissue zone while the flexible, elongate body is in vivo.

In another embodiment, the method further includes removing at least substantially all fluid present in the guarded zone through an aspiration lumen that extends between the proximal zone and the guarded zone. In a preferred embodiment, the method further includes retaining an amount of fluid removed from the guarded zone for analysis, biopsy, or both. In yet another embodiment, the method further includes ablating tissue in the guarded zone. In a preferred embodiment, the ablating and obtaining an image occur sequentially. In an alternative preferred embodiment, the ablating and obtaining an image occur concurrently.

In a third aspect, the disclosure encompasses a method for treating a tissue zone in a patient including by inserting from a proximal zone, a flexible, elongate body including first and second inflatable zones that are inflatable in vivo, to a distal position in a patient's vessel; inserting a treatment lumen that extends from the proximal zone to a distal portion of the flexible, elongate body that is distal to the first and second inflatable zones and adjacent the tissue zone to be treated; inflating at least one of the first and second inflatable zones sufficiently so as to block the vessel; and then treating the tissue zone with a therapeutic agent administered through the treatment lumen while at least one of the first and second inflatable zones is inflated.

In one embodiment, the therapeutic agent provided is selected to include oxygenated particles in an amount sufficient to provide oxygen to the patient distal to the flexible, elongate body. In another embodiment, the therapeutic agent is selected to include a dissolution agent sufficient to dissolve at least a portion of a dissolvable material adjacent the tissue zone. In yet a further embodiment, the tissue zone is selected from at least one of a vascular tissue, an esophageal tissue, a respiratory passage tissue, or an intestinal tissue, or a combination thereof. In one preferred embodiment, the method further includes providing an imaging component disposed in a guarded zone defined by a region between the first and second inflatable zones; providing through an irrigation lumen, which extends between the proximal zone and the guarded zone, an imaging fluid that is adapted to conduct a signal therethrough from the imaging component; and obtaining an image of the tissue zone with the imaging component. In a preferred embodiment, the method further includes removing at least substantially all fluid present in the guarded zone through an aspiration lumen that extends between the proximal zone and the guarded zone. In one embodiment, obtaining the image and the treating are concurrent. In another embodiment, obtaining the image and the treating are sequential and the flexible, elongate body is repeatedly advanced to dispose the imaging component adjacent the treated tissue before obtaining an image.

In a fourth aspect, the disclosure encompasses an in vivo imaging system including the imaging device described above; an interface module configured to connect with the imaging component; and an image processing component in communication with the interface module.

In a fifth aspect, the disclosure encompasses a method of forming an imaging device which includes providing a flexible, elongate body having proximal portion and a distal portion; and disposing within the flexible, elongate body an imaging system which includes: a first balloon assembly in a distal position, which includes a first balloon and a first connection lumen that extends from the proximal portion into the first balloon to permit transfer of a fluid therebetween so as to independently inflate or deflate the first balloon; a second balloon assembly in a proximal position relative to the first balloon assembly, which second balloon assembly includes a second balloon and a second connection lumen that extends from the proximal portion into the second balloon to permit transfer of a fluid therebetween so as to independently inflate or deflate the second balloon; a guarded zone disposed between the first and second balloon assemblies that is coupled to at least a first guarded zone lumen that extends from the guarded zone to the proximal portion; and an imaging component that is disposed in the guarded zone and that is configured to image an adjacent tissue zone of a patient.

Additional aspects, features, and advantages of the present disclosure will become apparent from the following detailed description. It should be understood that different embodiments may be alternative or additional, and that various embodiments discussed above can be combined in various ways.

BRIEF DESCRIPTION OF THE DRAWINGS

The present disclosure is best understood from the following detailed description when read with the embodiments, or examples, illustrated in the accompanying figures. It is emphasized that various features are not necessarily drawn to scale. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

Illustrative embodiments of the present disclosure, which form part of the present specification, will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Specific examples of components and arrangements are described below to simplify the present disclosure. These are, of course, merely examples and are not intended to be limiting. Any alterations and further modifications to the described devices, systems, and methods, and any further application of the principles of the present disclosure are fully contemplated and included within the present disclosure as would normally occur to one of ordinary skill in the art to which the disclosure relates. In particular, it is fully contemplated that the features, components, and/or methods described with respect to one embodiment may be combined with the features, components, and/or methods described with respect to other embodiments of the present disclosure. For the sake of brevity, however, the numerous iterations of these combinations will not be described separately.

Figure 1:
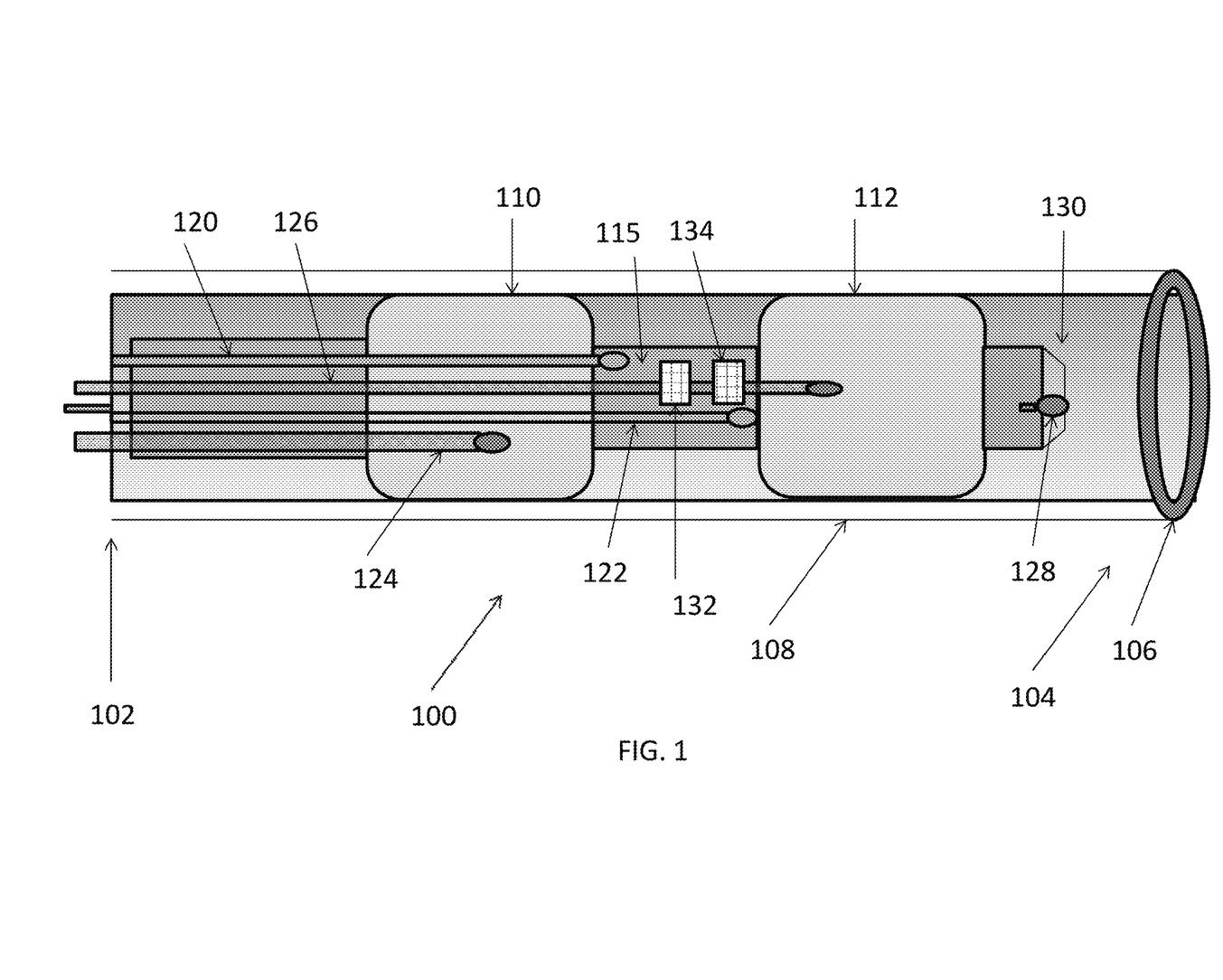
FIG. 1 is a diagrammatic schematic side view of exemplary in vivo imaging devices according to various embodiments of the present disclosure.

Referring to FIG. 1, shown therein is an imaging device 100 according to an embodiment of the present disclosure that includes a flexible, elongate body 108 having a proximal portion 102 and a distal portion 104 having a distal end 106. The flexible, elongate body 108 is typically formed of a plastic, polymer, or other flexible material, or combination thereof and designed to be flexible to effectively traverse a patient's vessels without damage. In one embodiment, the flexible, elongate body is a catheter, while in others it is adapted for respiratory passageways, etc.

The imaging device 100 includes in the distal portion 104 at least a first balloon assembly 110 and a second balloon assembly 112, each of which includes a balloon and respectively, a first connection lumen 126 and a second connection lumen 124. The first and second connection lumens 124, 126 may be used to transfer a fluid, which may be a gas or a liquid, between the proximal portion and each balloon. In low risk operations where the balloon will is unlikely to tear, a gas may be used, while a liquid is preferred in any use where the fluid might escape. These may be inflated sufficiently as shown to prevent the imaging device 100 from moving in vivo during imaging, treatment, or both, and then deflated sufficiently to advance the imaging device 100 as desired. When the first and second balloon assemblies 110, 112 are inflated, they define a guarded zone 115 disposed therebetween in the flexible, elongate body 100. The guarded zone 115 is coupled to at least a first guarded zone lumen 120 that extends from the guarded zone to the proximal portion. This first guarded zone lumen 120 may be used to transfer fluid between the guarded zone 115 and the proximal portion 102. The imaging device 100 may also include a guidewire lumen 130 that extends from the distal portion to at least a position distal to the second balloon assembly to facilitate advancement of the flexible, elongate body 108.

The imaging device 100 can also include one or more connectors therein (not shown) in one embodiment that connect between a proximal portion and the imaging component 132 in the guarded zone 115. Optionally, but preferably, the guarded zone is also coupled to at least a second guarded zone lumen 122. In this embodiment as shown, the first guarded zone lumen can be used to irrigate and the second guarded zone lumen can be used to aspirate fluid(s) between the guarded zone 115 and the proximal portion 102. When desired, this can advantageously permit removal of a portion of the blood in the guarded zone 115 and optionally but preferably replace it with an imaging fluid that is suitable for the type of imaging to be conducted by the imaging component 132. The imaging fluid can be any agent that permits high quality imaging, such as water, saline, or another irrigant that is a solution or otherwise has sufficiently few particles of a size that collectively cause interference with the imaging component 132 when in operation, e.g., blood. The imaging fluid is preferably substantially or entirely free of particles or other distortion-causing components, such as blood cells, ablated material, gaseous bubbles, or a combination thereof. Preferably, the entire guarded zone is replaced with an imaging liquid, or with suitable blood after imaging is completed, to avoid leaving any gas bubbles behind in the vessel that could cause patient complications. The imaging component 132 may be disposed in the guarded zone 115 in various positions using various techniques. As shown, the imaging component is coupled to an outside surface of the second connection lumen as it passes through the guarded zone 115. In other exemplary embodiments (not shown), the imaging component can be coupled to the first or second guarded zone lumens 120, 122, arranged about an inner surface of the flexible, elongate body 108, coupled to one of the balloons or connected between the balloons of the first and second balloon assemblies 110, 112, or coupled to the guidewire lumen as it passes through the guarded zone.

The imaging component 132 can be used to image the interior tissue of a patient's vessel, such as a vascular region, respiratory region (e.g., nasal or bronchial passage), digestive vessel (e.g., esophagus, intestine, etc.), or the like. Various types of imaging components may be used. One example of a preferred imaging component 132 is an OCT device or a high-resolution ultrasound device. In another form, the imaging component 132 can collect information for spectroscopy or photo acoustic imaging. A forward looking device that scans forward into the vessel rather than outward from the axis towards the walls of the vessel can also be used as an alternative or in addition to one that images perpendicularly to the longitudinal axis of the flexible, elongate body 108. In one aspect, a forward-looking imaging system may be positioned distal from balloon assembly 112 to assist with positioning the body 108 (such as a catheter) while the imaging component 132 is included in the guarded zone 115. When the imaging component 132 is rotational, it is typically operably connected to a distal end of a driveshaft, which may be included in a driveshaft lumen or be disposed in the first guarded zone lumen 220 with sufficient additional room for a fluid to be transferred through the lumen at the same time. In one preferred aspect, the driveshaft is disposed along with a liquid lubricant in the lumen 220, which minimizes friction and heat from the driveshaft during rotational operation. When the imaging component 132 is a solid-state device, also known as a phased-array, a plurality of ultrasound transducers are distributed around the circumference of the imaging component 132 and connected to a set of transducer controllers adapted to transmit an ultrasound pulse and receive the echo signal in a defined pattern. By stepping through a sequence of transmit-receive pairs, the solid-state ultrasound system can synthesize the effect of a mechanically scanned transducer element, but without moving parts.

The imaging component 132 disposed in the guarded zone 115 is configured to image an adjacent tissue zone of a patient. The flexible, elongate body 108 joins at least the first and second balloon assemblies 110, 112, the guarded zone 115, and the imaging component 132. In an optional, but preferred embodiment, the imaging device 100 also includes a distal lumen 128, which can be used to deliver a therapeutic agent to a location distal to the first and second balloon assemblies 110, 112 even while inflated. Any available therapeutic agent may be delivered, but preferably the distal lumen 128 is of a comparable size to the other lumens present. In one preferred embodiment, the therapeutic agent includes a gas-filled agent, preferably an oxygenated agent, such as oxygen-containing particles. Distal oxygenation via introduction of oxygen, such as oxygen-containing or other gas-containing particles to deliver oxygen or another gas to a location distal to the flexible, elongate body 100 while one or more of the inflatable zones 110, 112 is inflated enough to restrict or eliminate blood flow while inflated, can extend the time available for imaging using imaging component 132 or for any other reason. (See, e.g., "Injecting Oxygen Directly Into The Bloodstream Could Save Suffocating Patients," *Pop Sci.*, Jun. 27, 2012, http://www.popsci.com/science/article/2012-06/injecting-oxygen-filled-microparticles-bloodstream-could-buy-half-hour-suffocating-patients, which is incorporated herein in its entirety by express reference thereto.)

Another therapeutic agent that can be used in the guarded zone 115 or through the distal lumen 128 is a dissolving agent of one or more materials, e.g., acids, etchants, or the like, or any combination thereof, that can be used to dissolve deposits in the patient's tissue zone. Therapeutic agents may be administered in sequence, as well, to treat a newly exposed material in a tissue zone. Ablation or previous treatment with a dissolving agent may expose new material in the tissue zone, which may differ from previously removed dissolvable (or ablatable) material and may require a different therapeutic agent to most effectively continue treatment. In another embodiment (not shown), the distal lumen 128 or another lumen can extend from the proximal portion 102 to the guarded zone 115 to deliver a therapeutic agent to the guarded zone 115.

In another embodiment, an ablation device 134 is included in the guarded zone. The ablation device 134 can be coupled to a therapeutic lumen or at a distal end of the distal lumen 128 (each not shown) if desired, or preferably can be coupled to the second guarded zone lumen 122 that is used for aspiration. The ablation device 134 can effectively be disposed in the guarded zone 115 or distal to the distal balloon assembly 112 and coupled to the same type of components as noted herein for coupling the imaging component 132. The ablation device 134 and imaging component 132 can be disposed on the same or different part of the imaging device 100. In addition, or in place of removal of fluid in the guarded zone 115, the second guarded zone lumen 122 can be used to remove material loosened by the ablation device 134 when disposed in the guarded zone 115, as is preferred, to increase clarity of any additional imaging conducted with the imaging component 132. The ablation device 134 may use any available ablation method or component, including without limitation one or more lasers, electrical/cauterization, RF, ultrasound, and other suitable energy. Additional clear fluid, or remediated aspirated fluid having ablated, dissolved, or other material that has since been removed, can be irrigated into the guarded zone 115 through the first guarded zone lumen 120 or otherwise adjacent the ablation device 134 for further treatment.

Figure 2:
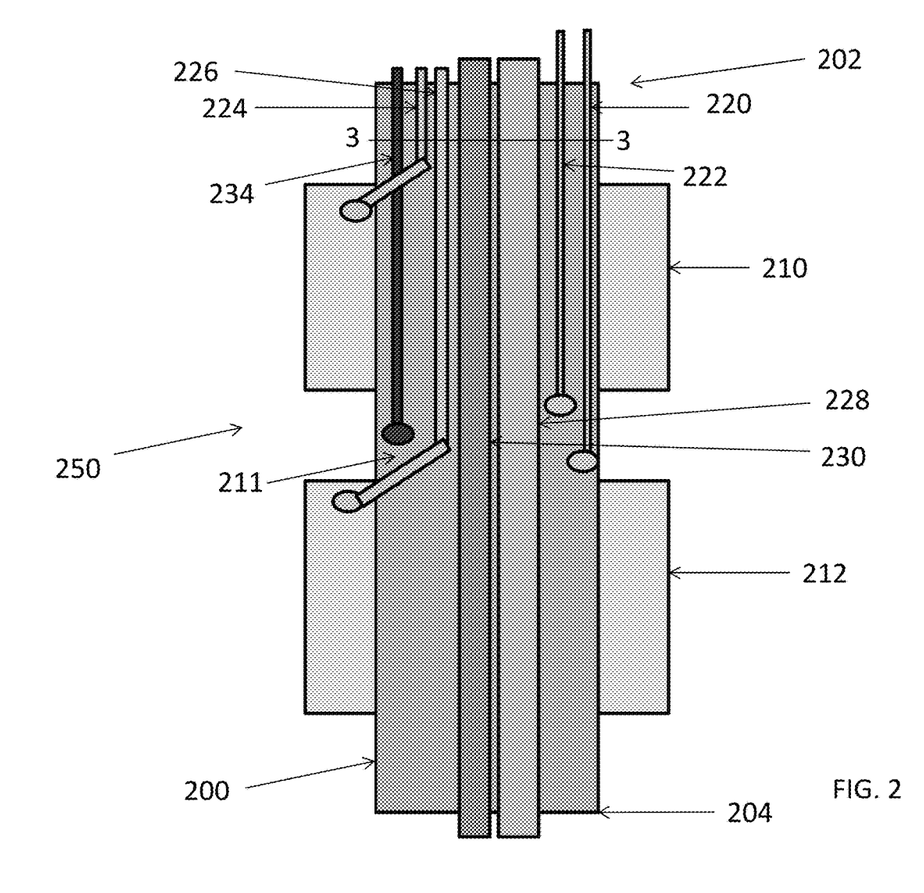
FIG. 2 is a diagrammatic schematic, partial cutaway side view of a distal portion of an imaging device according to an embodiment of the present disclosure.

Referring to FIG. 2, a distal section of the device 250 includes various lumens in various embodiments of the present disclosure. The integrated imaging and therapeutic device 250 shown here includes a flexible, elongate body 200 that joins or at least retains these various lumens. The flexible, elongate body 200 can be advanced in vivo to a tissue zone in a patient through use of a guidewire 230 that extends from a distal portion to at least a position distal to the second balloon assembly. In one embodiment, the guidewire extends through a guidewire lumen 230. As shown, a distal lumen 228 delivers a therapeutic agent from a proximal location 202 to a distal location 204 past the two balloon assemblies 210, 212. The first and second balloon assemblies 210, 212 can be inflated and deflated through dedicated first and second connection lumens 224, 226, respectively. A first guarded zone lumen 220 is included, although the optional but preferred second guarded zone lumen 222 is depicted as well. When both first and second guarded zone lumens 220, 222 are included, one may be adapted to irrigate the guarded zone 211 between the first and second balloon assemblies 210, 212 while the other may be adapted to aspirate the guarded zone 211.

Additionally, as shown, a connection media lumen 234 may be included. The connection media lumen 234 may include one or more electrical connectors, for example, to provide power to an imaging component, ablation component, or other equipment (not shown) in the guarded zone between the first and second balloon assemblies 210, 212. The one or more electrical connectors in the connection media lumen 234 may facilitate transmission of control signals to the imaging or ablation component, or both, as well as transmission of collected imaging information from the imaging component to a proximal position 202 for further processing and/or analysis. For example, one electrical connector could be a microcable having a braided exterior with a plurality (e.g., 7) individual insulated electrical conductors. The connection media lumen 234 may additionally or alternatively include one or more optical fibers, particularly where the imaging component 132 is adapted for optical coherence tomography, infrared, or other light-based imaging. In some embodiments, the connection media lumen 234 extends through the guarded zone and joins the imaging component 132, the optional ablation device 134 when present, or both. The processing system typically remains outside of the patient. The processing system uses the data received from the imaging component 132 to create an image. The image can be displayed to a medical professional in real time, for example, as the flexible, elongate body moves through the patient's vessel or as in situ treatment progresses. This allows the medical professional to find various occlusions or other irregularities that may exist throughout the patient's vessel. The number of wires, cables, or optical fibers typically depends on the type of imaging component and the manner in which data is transferred (or stored for analysis after removal of the device) from the imaging component to the external processing system(s).

In one embodiment (not shown), one or more of the lumens such as the connection media lumen 234 may be overmolded partially or entirely into the flexible, elongate body 200. The connection media lumen 234 may be or may include one or more electrical leads that extend between the proximal portion and the imaging component in the guarded zone. Although not shown, when any component such one or more electrical leads is built into part of the flexible, elongate body 200, the electrical leads may define their own connection media lumen 234.

Figure 3:
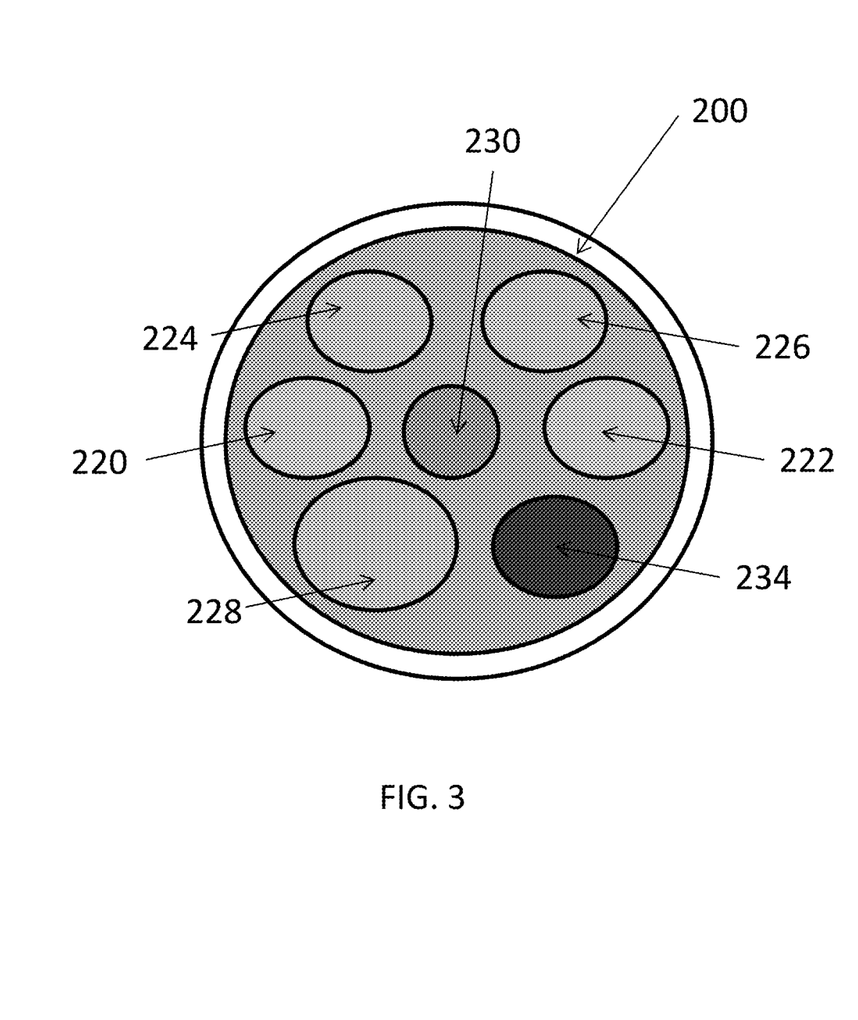
FIG. 3 is a cross-sectional view taken along line 3-3 of a distal portion of the imaging device shown in FIG. 2, according to an embodiment of the present disclosure.

FIG. 3 is a cross-section of a proximal cross-section of the distal portion of the flexible, elongate body 200 shown in FIG. 2. As shown, the cross-section includes a guidewire lumen 230, a distal port lumen 228, first and second guarded zone lumens 220, 222 that can be used for irrigation and aspiration of fluids (which can also be referred to as guarded zone fill and guarded zone vent lumens), first and second connection lumens 224, 226 that extend between a proximal portion of the flexible, elongate body 200 to a distal position coupled with the first and second balloon assemblies, respectively. Also included is a connection media lumen 234, which although not shown can include one or more electronic conduction wires optionally with additional other connections therein. The one or more electronic conduction wires when included in a preferred embodiment provide electric power to the imaging component, and to the optional ablation device when present. The one or more electronic conduction wires also facilitate transmission of data signals between the proximal portion or end, where an interface module may be disposed to receive and process data signals relating to the imaging or operation of the ablation device and any associated sensors included therewith in the flexible, elongate body.

In one embodiment, one of the first and second guarded zone lumen 220, 222 is used to provide a therapeutic or diagnostic agent to the tissue zone in the guarded zone 211. A preferred diagnostic agent includes an irrigant fluid, preferably a liquid. The other of the first and second guarded zone lumens is used to aspirate blood or other distortion-causing fluid from the guarded zone 211. In one embodiment, the distortion-causing fluid includes ablated material removed from tissue with the ablation device 134. When one of the first and second guarded zone lumens 220, 222 administers a therapeutic agent as previously discussed, the imaging component and guarded zone 211 may be adjacent to the tissue zone being treated and imaged. In an alternative embodiment, the tissue zone being treated may be distal to the flexible, elongate body 200, which may be advanced after treatment to arrange the guarded zone near the treated tissue zone. This is an exemplary technique that can permit continuous treatment and imaging, because the imaging will occur shortly after treatment as the flexible, elongate body 200 is advanced.

In various embodiments directed to the present guarded zone imaging devices, a distal lumen may be incorporated to deliver a therapeutic agent and an imaging component or imaging system to accurately access, assess, and treat vessels and/or other tubular structures within a patient. For example, embodiments of the present disclosure are configured to dissolve deposits in a patient vessel or to deliver oxygenated particles to extend the time for in-depth imaging as discussed herein. Some of the embodiments disclosed herein comprise dual balloon assemblies that incorporate an imaging component 132 such as, by way of non-limiting example, transducers and optical devices operable to perform sensing modalities such as IVUS, optical coherence tomography (OCT), photo acoustic inspection, infrared imaging, and spectroscopy. Preferably, the imaging is OCT or high-frequency ultrasound or IVUS, i.e., at a frequency of greater than about 40 MHz to about 80 MHz, more preferably 45 MHz to about 75 MHz. In some embodiments, the imaging component 132 may be oriented generally perpendicular to the longitudinal axis of the flexible, elongate body 100 for side looking imaging while other embodiments may employ axially oriented imaging sensors that provide forward looking imaging ahead or to the side(s) of the distal balloon assembly. Thus, the embodiments disclosed herein may advantageously allow a medical professional to access, assess, and treat diseased vessels and related tissues in a patient, with more imaging visibility and over a longer time in vivo than offered by some prior art catheters and similar devices.

Figure 4:
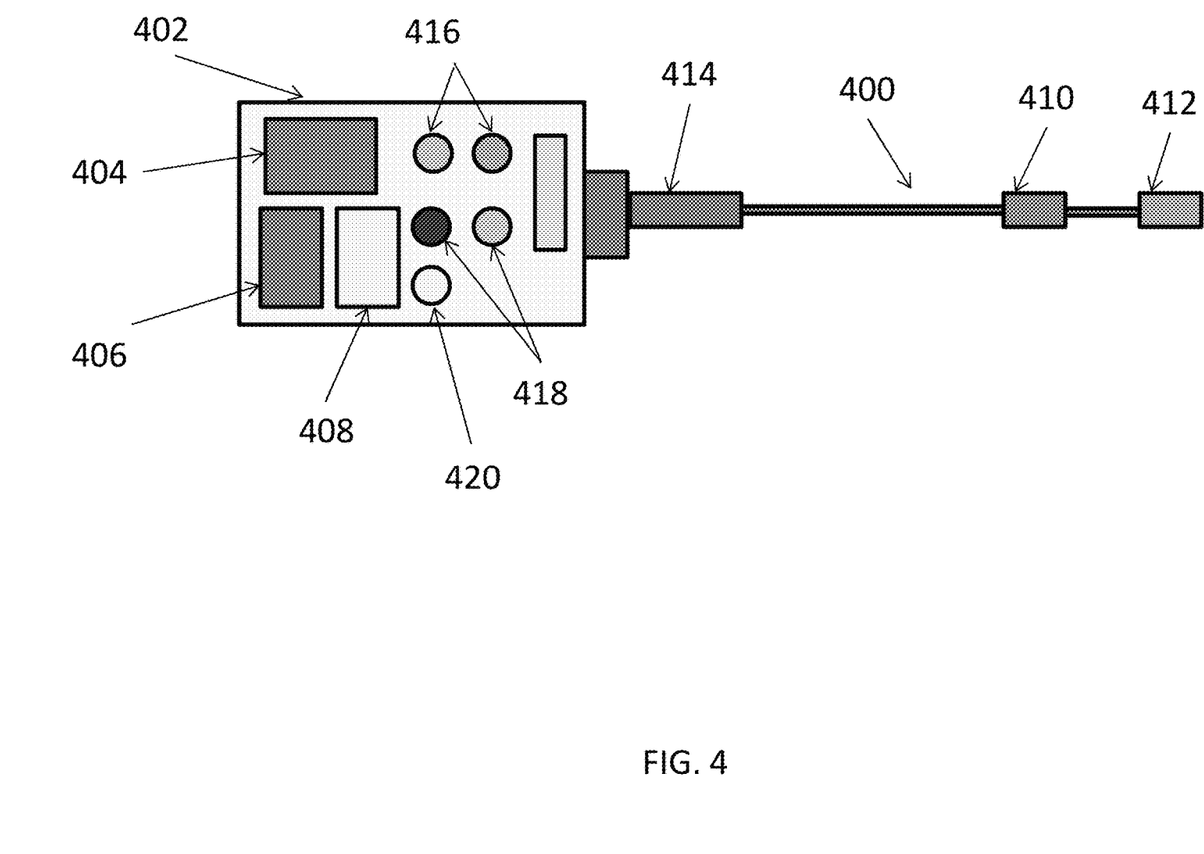
FIG. 4 is a diagrammatic schematic top down view of a fluid controller module according to an embodiment of the present disclosure.

An exemplary fluid controller module 402 is shown in FIG. 4 operatively coupled with a catheter 400 having first and second balloon assemblies 410, 412 in one aspect of the invention. While the fluid controller module 402 is optional, it may be preferred in some embodiments. The fluid controller module 402 may be arranged to include one or more of the following: a reservoir 406 for an irrigating fluid and/or therapeutic agent; a reservoir for an oxygenating fluid 408. To be clear, in this embodiment, the therapeutic agent may be a dissolving agent and the oxygenating agent is a separate component (i.e., an additional therapeutic agent). A timer/controller 404 may manage the valve sequences to automate or partially automate the fluid control at set times after initiation or under control of a medical professional. A fluid reservoir 414 may be included, either to store additional irrigating fluid, therapeutic agent, or oxygenating fluid, preferably separately in sub-reservoirs (not shown) or in sequence, or simply to provide the fluid in a location more closely adjacent to the catheter 400 itself for any or all of these fluids, which may facilitate control when inserting a specific amount therein. The fluid controller module 402 may also preferably include valves to facilitate control, which may alternatively include connectors to plug in external fluid flow supply. The valves may include, for example, balloon fill valves 416, guarded zone fill/purge (irrigate/aspirate) valves 418, oxygenating fluid valve 420, or the like. Preferably, pressure monitoring instrumentation, fluid flow monitoring instrumentation, or both may be included, such as in the depicted pressure and flow monitoring instrumentation panel 422. Various other configurations may be envisioned in different embodiments despite not being depicted in FIG. 4.

Methods of Use: Imaging, Treatment, and Integrated Imaging and Treatment

The imaging component can take and store images taken within a living body for retrieval after removal of the imaging device from the patient. Preferably, however, the imaging component is operatively coupled with an interface system external to the patient. It is possible to operatively couple these to transmit signals, such as by RF or other mechanisms, but preferably data signals representative of imaging information collected by the imaging component are transmitted via the connection media lumen between the imaging component and the proximal portion where the interface system may process such signals to provide images readily understandable by a medical professional, and in some embodiments even the patient.

Preferably, the first and second balloons are deflated at least sufficiently or entirely to facilitate advancing the flexible, elongate body in vivo. It should be understood that by "advancing" it is typically meant the catheter is moved into the body away from a point of access into the body. In one embodiment, however, the term also means the catheter may be moved proximally towards or distally from the point of access.

A tissue zone in a patient may be imaged by inserting a flexible, elongate body that includes first and second inflatable zones that are inflatable in vivo, and an imaging device disposed in a guarded zone defined by a region between the first and second inflatable zones, from a proximal position or zone to a distal position adjacent a tissue zone to be imaged. By disposing an imaging component in such a guarded zone, this permits the blood or other fluid to be replaced with an imaging fluid that is preferably clear (to the imaging component signals) irrigated through an irrigation lumen, which extends between the proximal zone and the guarded zone, and then obtaining an image of the tissue zone with the imaging component of the device. This advantageously can provide clearer images, particularly using imaging modalities that provide poor quality without the proper imaging fluid, such as OCT and high-frequency ultrasound. The imaging can be achieved with rotational ultrasound transducers or optical fiber or reflector, or with a phased-array arrangement of such equipment as part of the imaging component. Preferably, one or more images so obtained do not contain visible distortion at normal magnification, such as speckles. Multiple images can be obtained while the flexible, elongate body is fixed in place, or while it is advanced so that the imaging device is adjacent to one or more additional tissue zones. In a preferred embodiment, at least substantially all, or all, fluid present in the guarded zone is removed through an aspiration lumen that extends between the proximal zone and the guarded zone. This can permit removal of distortion-causing fluid, which may be fluid including ablated material, blood, etc. or a combination thereof. In one embodiment, the removed fluid can be retained for analysis, biopsy, or both.

Either concurrent with, or in various sequences with, the imaging, the disclosure includes embodiments that involve treating the patient's tissue zone by providing at least one therapeutic agent through a treatment lumen that extends from the proximal zone to the guarded zone or to a position distal both the first and second balloon assemblies. Preferably, this occurs with the flexible, elongate body in vivo to avoid time-consuming imaging, removal, treatment, and then re-insertion for additional imaging. Treatment can take various forms as disclosed herein, including providing oxygenated particles, such as nanoparticles, to a position distal to the entire imaging device to provide oxygen to tissues that would otherwise lack oxygen due to the cessation of fluid flow past the inflated zones of the flexible, elongate body when inflated. In a vascular vessel, this can permit oxygenation of tissues to extend the time for imaging or other treatment.

In another embodiment, an obtained image or images can be analyzed to identify a dissolvable material in the tissue zone, and at least one therapeutic agent can be selected to treat the dissolvable material concurrently or in sequence. This may be referred to as selective dissolution, which is facilitated by constant, high resolution imaging to help analyze the materials to be dissolved or removed (e.g., through ablation) in the tissue zone. In one embodiment, the process can be repeated as needed by analyzing, selecting, and treating in sequence to remove a plurality of dissolvable materials from the tissue zone while the flexible, elongate body is in vivo. In a further aspect, the processing system includes a database of tissue information allowing received signals to be compared to perform tissue characterization. Tissue characterization information can be displayed to the user to access the progress of treatment and any potential adverse events. Thus, as each dissolvable material is identified by imaging, an appropriate therapeutic agent can be provided to the tissue zone to be treated, either in the guarded zone adjacent the imaging component or distal to the entire device.

In another embodiment, which may be used in conjunction with the imaging component, with or without associated administration of a therapeutic agent, an ablation device may ablate tissue in the guarded zone. This ablation may occur concurrently or sequentially with imaging. Various sequences can be used, such as imaging followed by ablation; imaging followed by ablation repeatedly; imaging, ablation, and imaging to confirm success; etc. Similarly, other sequences can include imaging, administration of a therapeutic agent, imaging; imaging, administration of a therapeutic agent, ablation, imaging; imaging, administration of a therapeutic agent, imaging, administration of a second therapeutic agent, which may be the same or different; etc. When the therapeutic agent includes one or more dissolvable materials, these may be administered in the guarded zone through the first guarded zone lumen or otherwise, as well as at a position distal to the flexible, elongate body, or both. The tissue zone to be imaged, or imaged and treated (including ablation), is selected from at least one of a vascular tissue, a respiratory passage tissue, or a digestive tissue (including esophageal, intestinal, etc.), or a combination thereof. When imaging and treating are concurrent, additional similar sequences can be used. For example, the imaging may be constant and the treatment may be administered with the outcome imaged to evaluate for additional treatment. When the image and the treating are sequential and the treating occurs at a distal location to the flexible, elongate body, the body may be repeatedly advanced after each treatment to dispose the imaging component adjacent the treated tissue before obtaining one or more images.

In vivo imaging systems are also included in the disclosure herein. These may include an imaging device that is adapted to intravascular, intra-bronchial, intra-nasal, or any other suitable vessel imaging. Preferably, the device is an integrated imaging and treatment device. In non-fluid filled passages, the guarded zone may be filled with an irrigant fluid, such as saline, to facilitate transmission of signals. For example, introduction of fluid temporarily to a passageway in the guarded zone can permit ultrasound waves to propagate from the transducer(s) to the tissue of interest, and the fluid can later be removed concurrently or sequentially with removal of the catheter from the tissue zone. The imaging system thus includes the imaging device along with at least an interface module configured to connect with the imaging device, and image processing component (software, hardware, or both) in communication with the interface module. The interface module and image processing are typically positioned ex vivo and connected electronically or optically to the imaging component in the imaging device.

Methods of forming the imaging devices herein are also included as described herein and as would be readily understood by those of ordinary skill in the art based on the imaging devices and systems, and related guidance, provided herein.

Persons of ordinary skill in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An imaging device having a proximal portion and proximal end, and a distal portion and distal end, which comprises:
   a first balloon assembly in a distal position, which comprises:
      a first balloon; and
      a first connection lumen that extends from the proximal portion into the first balloon to permit transfer of a fluid therebetween so as to independently inflate or deflate the first balloon;
   a second balloon assembly in a proximal position relative to the first balloon assembly, which second balloon assembly comprises:
      a second balloon; and
      a second connection lumen that extends from the proximal portion into the second balloon to permit transfer of a fluid therebetween so as to independently inflate or deflate the second balloon;
   a guarded zone disposed between the first and second balloon assemblies that is coupled to at least a first guarded zone lumen that extends from the guarded zone to the proximal portion;
   an imaging component that is disposed in the guarded zone and that is configured to image an adjacent tissue zone of a patient; and
   a flexible, elongate body comprising a perimeter bounding at least the first and second balloon assemblies, the guarded zone, and the imaging component, wherein the first and second balloon assemblies are, when inflated, disposed within the perimeter of the flexible, elongate body.

2. The imaging device of claim 1, wherein the imaging component is coupled to a connection media lumen that extends from the proximal portion to a second position within the guarded zone.

3. The imaging device of claim 2, wherein the connection media lumen encompasses at least one electrical conduction wire: to provide electrical power to the imaging component, to transmit data signals between the imaging component and the proximal portion, or both.

4. The imaging device of claim 2, wherein the imaging component comprises at least a portion of an optical coherence tomography device including an optical fiber or reflector and further comprising an optical fiber disposed in the connection media lumen.

5. The imaging device of claim 1, further comprising a second guarded zone lumen wherein the first guarded zone lumen permits transfer of a fluid into the guarded zone and the second guarded zone lumen permits transfer of a fluid from the guarded zone to a position distal to at least one of the first and second balloons.

6. The imaging device of claim 1, wherein the imaging component comprises at least one ultrasound transducer.

7. The imaging device of claim 6, wherein the ultrasound transducer is adapted to operate in a high frequency range of about 40 MHz to about 80 MHz.

8. The imaging device of claim 1, wherein the first guarded zone lumen is adapted to deliver a therapeutic or diagnostic agent to the tissue zone.

9. The imaging device of claim 1, which further comprises an ablation device disposed in the guarded zone.

10. The imaging device of claim 1, which further comprises a distal port lumen that extends from the proximate portion to a position distal the first and second balloon assemblies.

11. The imaging device of claim 10, wherein the distal port lumen is configured to deliver a therapeutic or diagnostic agent to the distal end when at least one of the first and second balloons is inflated.

12. A method for imaging a tissue zone in a patient which comprises:
   inserting from a proximal zone, a flexible, elongate body comprising first and second inflatable zones that are inflatable in vivo and an imaging component disposed in a guarded zone defined by a region between the first and second inflatable zones and by a perimeter of the flexible elongate body, to a distal position adjacent a tissue zone to be imaged, wherein the first and second inflatable zones, when inflated, are disposed within the perimeter of the flexible, elongate body;
   providing through an irrigation lumen, which extends between the proximal zone and the guarded zone, an imaging fluid that is adapted to conduct a signal therethrough that is emitted by the imaging component; and
   obtaining an image of the tissue zone with the imaging component.

13. The method of claim 12, wherein the obtaining the image is selected to comprise optical coherence tomography or high-resolution ultrasound imaging at a frequency range of about 40 MHz to about 80 MHz.

14. The method of claim 13, wherein the imaging component is selected to comprise a rotational element.

15. The method of claim 13, wherein the imaging component is selected to comprise a phased-array.

16. The method of claim 13, wherein at least one of the images obtained does not contain visible distortion at normal magnification.

17. The method of claim 13, which further comprises removing at least substantially all fluid present in the guarded zone through an aspiration lumen that extends between the proximal zone and the guarded zone.

18. The method of claim 17, which further comprises retaining an amount of fluid removed from the guarded zone for analysis, biopsy, or both.

19. The method of claim 13, which further comprises ablating tissue in the guarded zone.

20. The method of claim 19, wherein the ablating and obtaining an image occur sequentially.

21. The method of claim 19, wherein the ablating and obtaining an image occur concurrently.

22. The method of claim 12, wherein the obtaining the image is repeatedly conducted as the flexible, elongate body is advanced so that the imaging component is adjacent to one or more additional tissue zones.

23. The method of claim 12, which further comprises treating the tissue zone by providing at least one therapeutic agent through a treatment lumen that extends from the proximal zone to the guarded zone.

24. The method of claim 23, wherein the treating is concurrent with the obtaining an image.

25. The method of claim 23, which further comprises analyzing an obtained image to identify a dissolvable material in the tissue zone, and selecting the at least one therapeutic agent to treat the dissolvable material.

26. The method of claim 25, which further comprises repeating the analyzing, selecting, and treating to remove a plurality of dissolvable materials from the tissue zone while the flexible, elongate body is in vivo.

27. A method for treating a tissue zone in a patient which comprises:

inserting from a proximal zone, a flexible, elongate body comprising first and second inflatable zones that are inflatable in vivo, to a distal position in a patient's vessel;

inserting a treatment lumen that extends from the proximal zone to a distal portion of the flexible, elongate body that is distal to the first and second inflatable zones and adjacent the tissue zone to be treated;

inflating at least one of the first and second inflatable zones, wherein the at least one of the inflatable zones is disposed within a perimeter of the elongate body; and then treating the tissue zone with a therapeutic agent administered through the treatment lumen while at least one of the first and second inflatable zones is inflated.

28. The method of claim 27, wherein the therapeutic agent provided is selected to comprise oxygenated particles to provide oxygen to the patient distal the flexible, elongate body.

29. The method of claim 27, wherein the therapeutic agent is selected to comprise a dissolution agent sufficient to dissolve at least a portion of a dissolvable material adjacent the tissue zone.

30. The method of claim 27, wherein the tissue zone is selected from at least one of a vascular tissue, an esophageal tissue, a respiratory passage tissue, or an intestinal tissue, or a combination thereof.

31. The method of claim 27, which further comprises providing an imaging component disposed in a guarded zone defined by a region between the first and second inflatable zones;

providing through an irrigation lumen, which extends between the proximal zone and the guarded zone, an imaging fluid that is adapted to conduct a signal therethrough from the imaging component; and obtaining an image of the tissue zone with the imaging component.

32. The method of claim 31, which further comprises removing at least substantially all fluid present in the guarded zone through an aspiration lumen that extends between the proximal zone and the guarded zone.

33. The method of claim 31, wherein the obtaining the image and the treating are concurrent.

34. The method of claim 31, wherein the obtaining the image and the treating are sequential and the flexible, elongate body is repeatedly advanced to dispose the imaging component adjacent the treated tissue before obtaining an image.

35. An in vivo imaging system comprising:
the imaging device of claim 2;
an interface module configured to connect with the imaging component; and
an image processing component in communication with the interface module.

36. A method of forming an in vivo imaging device which comprises:
forming a flexible, elongate body having a proximal portion and a distal portion; and
disposing within a perimeter of the flexible, elongate body an imaging system which comprises:
a first balloon assembly in a distal position, which comprises:
a first balloon; and
a first connection lumen that extends from the proximal portion into the first balloon to permit transfer of a fluid therebetween so as to independently inflate or deflate the first balloon;
a second balloon assembly in a proximal position relative to the first balloon assembly, which second balloon assembly comprises:
a second balloon; and
a second connection lumen that extends from the proximal portion into the second balloon to permit transfer of a fluid therebetween so as to independently inflate or deflate the second balloon;
a guarded zone disposed between the first and second balloon assemblies and the perimeter of the elongate body, wherein the guarded zone is coupled to at least a first guarded zone lumen that extends from the guarded zone to the proximal portion; and
an imaging component that is disposed in the guarded zone and that is configured to image an adjacent tissue zone of a patient.

* * * * *